United States Patent [19]

Shishov et al.

[11] Patent Number: 4,620,847
[45] Date of Patent: Nov. 4, 1986

[54] DEVICE FOR ADMINISTERING POWDERED SUBSTANCES

[75] Inventors: Nikolai M. Shishov; Vladimir E. Zelenetsky; Nadezhda A. Demina; Ivan M. Bondarev; Alexandr N. Cherny, all of Moscow; Valery A. Moskvitin, Belgorod-Dnestrovsky, all of U.S.S.R.; Evgeny E. Rylov, deceased, late of Moscow, U.S.S.R., by Nina Alexeevna Rybakova, administratrix

[73] Assignee: Vsesojuzny Nauchno-Issledovatelsky Institut Meditsinskikh Polimerov, Moscow, U.S.S.R.

[21] Appl. No.: 617,506

[22] Filed: May 6, 1984

[51] Int. Cl.[4] .............................. A61M 13/00
[52] U.S. Cl. ................... 604/58; 128/203.15; 222/325; 604/187; 604/243
[58] Field of Search .............. 604/58, 27, 36, 38, 604/187, 240, 243; 128/203.15; 222/490, 325, 209; 169/33

[56] References Cited

U.S. PATENT DOCUMENTS

| | | | |
|---|---|---|---|
| 2,518,522 | 8/1950 | Cimbura et al. | 222/325 |
| 2,518,523 | 8/1950 | Cimbura et al. | 222/325 |
| 2,525,742 | 10/1950 | Weiss et al. | 169/33 |
| 2,946,332 | 7/1960 | Sacks | 128/203.15 |
| 3,093,274 | 6/1963 | Galbierz | 222/325 |
| 3,858,583 | 1/1975 | Hallworth | 128/203.15 |
| 3,906,950 | 9/1975 | Cocoza | 128/203.15 |
| 3,949,751 | 4/1976 | Birch et al. | 128/266 |
| 4,017,007 | 4/1977 | Riccio | 604/58 |
| 4,082,095 | 4/1978 | Mendelson | 604/38 |

FOREIGN PATENT DOCUMENTS

| | | | |
|---|---|---|---|
| 607237 | 8/1948 | United Kingdom | 604/58 |
| 1436028 | 5/1976 | United Kingdom | |
| 615934 | 7/1978 | U.S.S.R. | |

OTHER PUBLICATIONS

"Device for Administering Medicinal Substance into Human Organism", I. M. Bondarev et al, *Meditsinskaiya Tekhnika–Journal of Medical Technology*, No. 6 (1976), pp. 17–18 (w/translation).

*Primary Examiner*—Richard C. Pinkham
*Assistant Examiner*—T. Brown
*Attorney, Agent, or Firm*—Fleit, Jacobson, Cohn & Price

[57] ABSTRACT

A device for administering powdered substances into deep-seated cavities of an organism includes a sprayer of powdered substances, a conveying line including a drainage pipe and a catheter, a hollow cylindrical body divided by a diametral partition and a cover, and a first sleeve positioned in the diametral partition and a second sleeve positioned in the cover. Both sleeves have openings that are coaxial with the conveying line.

2 Claims, 5 Drawing Figures

DEVICE FOR ADMINISTERING POWDERED SUBSTANCES

FIELD OF THE INVENTION

The present invention relates to surgical devices and, more particularly, it relates to devices for administering powdered substances.

This invention may be used for administering medicinal substances into human organism, in particular, into deep-seated cavities of the organism. This invention may be used to the maximum advantage in treating cavernous forms of tuberculosis, however, it may also be employed for treating a residual postresection cavity in the pleura or the empyema of the chest, or when giving emergency aid to spontaneous pneumothorax patients.

DESCRIPTION OF PRIOR ART

There is known a prior art device for administering powdered medicine into the body of a patient (cf., British Pat. No. 1,436,028, index of acceptance A 5 R 33 E).

Said prior art device comprises a chamber with a capsule of medicine accommodated therein and two coaxially arranged pipes connected to the capsule, one of said pipes being connected with a bottle for the delivery of air to the capsule while the other one of said pipes serves for injecting the powdered medicine into the patient's body cavity via mouth, nose, ears, through damaged tissue or wounds.

However, the structure of said prior art device does not permit of percutaneous administering of powdered substances into deep-seated cavities of the organism such as tuberculous cavern cavity.

There is further known a prior art device for administering powdered medicine into human organism, which comprises a container for medicinal preparation connected with a rubber bottle, and a pipeline connected with a metal trocar and catheter. In so doing, the trocar and catheter are arranged coaxially with a gap therebetween (cf., I. M. Bondarev, L. I. Zhigalina, A. N. Chernii, Device for Administering Medicinal Substance into Human Organism, Meditsinskaiya tekhnika-Journal of Medical Technology, No. 6, 1976, Moscow, pp. 17-18).

In the course of treatment, the skin and underlying tissues are punctured with the metal trocar including a tight-fitting stylet terminating in a piercing point. After that, the stylet is withdrawn from the trocar and replaced with a rigid catheter. The process of administering the medicinal preparation is performed from the container via catheter owing to an air pulse obtained by squeezing the rubber bottle. Excess air is removed from the focus of disease via clearance between the trocar and catheter walls and further via union located in the proximal portion of the trocar.

Said latter prior art device suffers from the following disadvantages:

the metal trocar is introduced into one and the same spot of the patient's body each time the preparation is administered (every 2-3 days throughout the entire period of the course of treatment, which may last for at least six months), this causing strong painful sensations;

in addition, the introduction of metal trocar into a cavity in the organism is always accompanied with X-ray treatment, which causes an increse in the irradiation dose received by the patient and personnel over the course of treatment;

the trocar in its proximal portion is made fast in a head with union, said head being provided with a groove for receiving a pin designed to lock the stylet in a preset position, which complicates the trocar structure;

it appears undesirable to remove bacteria-contaminated excess air from the focus of disease via union directly to the environment because the personnel may get the infection;

the structure of the device prevents the pipeline from being tightly joined with the catheter, this causing the formation of powder settling zones and the plugging of the catheter.

Besides that, the currently employed technology of manufacturing metal needles does not permit of attaining a higher grade of the desired roughness of the needle inner surface, which is likewise conducive to the plugging of the catheter with powder.

There is known a pulverizer of powdered substances, which comprises a hermetic cone-shaped glass container for powdered substance sealed at straight angles in a pipeline and connected with delivery means fashioned as a rubber bulb provided with an additional chamber. The narrow portion of the cone-shaped container has double walls with a space therebetween. The inner wall is provided with capillary openings while the space between the walls is connected to the additional chamber of the rubber bulb (cf., U.S.S.R. Inventor's Certificate No. 615,934, Int. Cl.$^2$ A 61 M 11/02, of 1978).

The disadvantages of said latter prior art device reside in a complicated structure and complex technology of manufacturing the powder container and delivery means. Because of this design, every individual device is to be manufactured manually. The manufacturing process is not susceptible to automation or mechanization.

Because of the absence of valves in the delivery means, the pipeline may be plugged with powder dur to the emergence of return air flow.

The powder may be drawn into connecting elements and delivery means and can only be removed after disassembling the entire device and cleaning its parts, which complicates the work of the medical personnel.

Moreover, such a pulverizer design is characterized by the possibility of frequent clogging of the pipeline with powder, which affects the efficiency of pulverization and reliability of operation because, upon squeezing the rubber bulb, part of the air flow supplied to the container from the smaller chamber transfers a small amount of powder to the pipeline where said powder is condensed by the air flow supplied from the bigger chamber of the bulb and moved via pipeline to the cavern.

Also known in the art is a device for administering medicine to human organism, which comprises a housing accommodating therein a capsule with medicine, one end of said housing being connected with air delivery means in the form of a rubber bottle with a built-in unidirectional valve accommodating thereinside a needle for puncturing the medicine capsule while the other end of the housing is connected with a detachable tip for the injection of powder (cf., U.S. Pat. No. 3,949,751, class 128-266, of 1976).

When using the latter prior art device, the capsule with medicinal preparation is placed inside the space of the housing and the latter is coupled with the detachable tip and delivery means. The rubber bottle is squeezed in the longitudinal direction: both end walls of the capsule are punctured by the needle. For pulverizing the medicinal preparation, the bottle is squeezed in the lateral direction. The air passes both inside and outside of the capsule.

After the bottle regains its initial shape, the valve is opened and air is supplied to the bottle.

However, said prior art device suffers from a number of disadvantages.

The provision of two holes in the capsule may lead to a lower pulverization efficiency because the air supplied to the capsule compacts the powder at the outlet hole. In addition, the puncturing of the end walls of the capsule is accompanied by the formation of burrs on which the powdered medicine tends to accumulate upon return air flow, said burrs also facilitating the clogging of the holes, which further affects the efficiency of administering the medicine.

Said latter prior art device fails to provide for reliable operation at the moment of spraying the powder in a deepseated cavity of the organism and, at the same time, attain a uniform and efficient pulverization of medicinal preparation.

SUMMARY OF THE INVENTION

It is an object of the present invention to provide a device for administering powdered substances, the use of which would ensure the possibility of repeated connection of the device to a tube introduced in the organism, without removing said tube from the patient's body throughout the course of treatment.

It is another object of this invention to provide a device that would eliminate the clogging of the conveying line with powdered substance.

It is one more object of the present invention to improve the reliability of the device operation.

Said and other objects of the invention are attained owing to the fact that a device for administering powdered substances into deep-seated cavities of the organism, comprising, series-connected, a sprayer of powdered substances provided with a cylinder and a piston movable inside said cylinder, and a conveying line which includes coaxially-arranged drainage pipe and catheter, according to the present invention, is also provided with means comprising a hollow cylindrical body with diametral partition and a cover, both said partition and said cover accommodating a sleeve with an opening coaxial with the conveying line for fitting the catheter and connecting the latter to the sprayer and to the drainage pipe.

It is expedient that the cover have in its bottom at least one opening closed with a bactericidal filter.

The herein disclosed device for administering powdered substances into the patient's organism makes for a considerable reduction of the overall duration of treatment and provides a possibility of its repeated use without performing any additional operations and without removing from the patient's body a tube introduced the first time the medicinal substance is administered.

The powdered medicinal substance does not accumulate in the device spaces, thereby facilitating considerably the device operation and improving its reliability.

The device of the invention is simple and readily adaptable to manufacture especially, when polymeric materials are employed.

BRIEF DESCRIPTION OF THE DRAWINGS

Other objects and advantages of the present invention will be made apparent upon considering the following detailed description of examplary embodiments thereof, with due reference to the accompanying drawings in which.

DETAILED DESCRIPTION OF THE INVENTION

Figure 1:
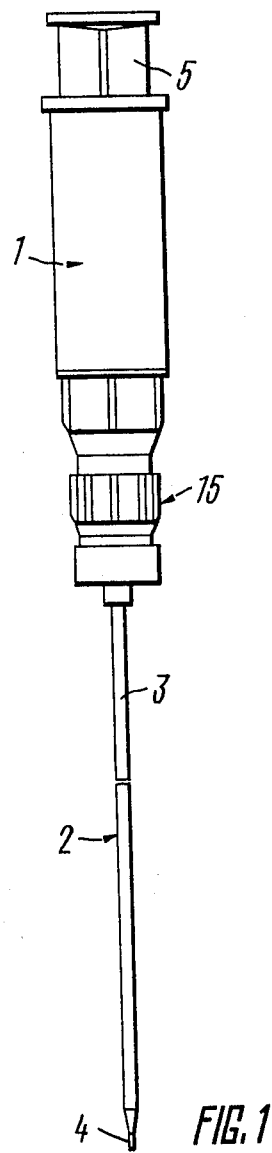
FIG. 1 is a general view of the device for administering powdered substances, according to the present invention.

Referring now to FIG. 1 of the accompanying drawings, the herein disclosed device for administering powdered substances into deep-seated cavities of the organism comprises, connected in series, a sprayer 1 and a conveying line 2 including a drainage pipe 3 and a catheter 4, said drainage pipe and catheter arranged coaxially with each other. The sprayer 1 includes a piston 5 (FIG. 1) and a cylindrical housing 6.

The sprayer 1 further includes an auxiliary housing 7 having a cylindrical portion 8 and a tapered portion 9 terminating in an outlet opening 10 and forming a diffusor. The housing 7 accommodates therein a container 11 with powdered substance being sprayed having an opening 12 directed towards the conveying line 2.

The outer surface of the container 11 (FIG. 2) is analogous with the inner surface of the housing 7 while the inner surface of the container has a smooth outline which rules out the possibility of formation of stagnant pockets upon spraying of the powdered substance. The container 11 is secured in position in the housing 7 with a clearance by means of longitudinal ribs 13 provided on the inner surface of the housing 7. The container 11 may be employed for one application, however, it is expedient that the container 11 should be adapted for repeated use by providing it with a detachable sealed cover 14.

The opening 12 of the container 11 and the opening 10 in the housing 7 are coaxial with the conveying line 2.

The ribs 13 on the housing 7 are made such as to ensure a guaranteed clearance between the openings 10 and 12.

The sprayer 1 is communicated with the conveying line 2 through the intermediary of means 15 (FIG. 1) said means comprising a cylindrical body 16 (FIG. 2) with a diametral partition 17 dividing it into chambers 18 and 19, and a cover 20.

Figures 2, 3, 4, 5:
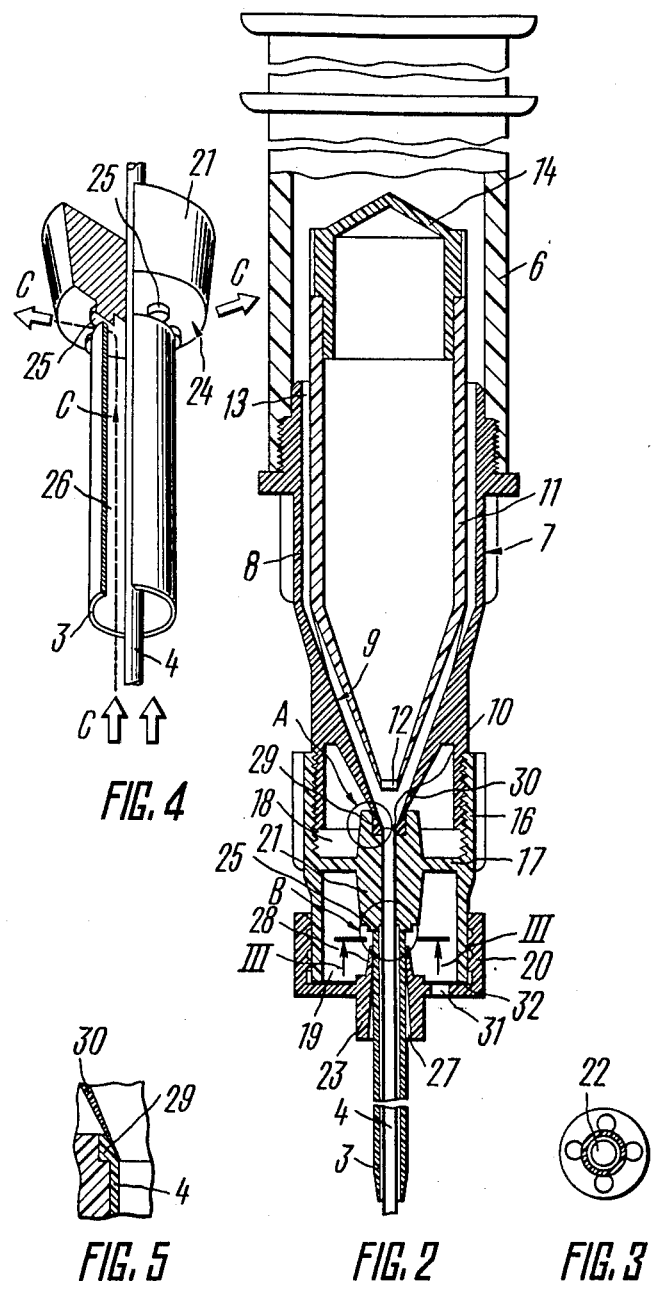
FIG. 2—ditto, in longitudinal section.
FIG. 3—ditto, a section taken along the line III—III of FIG. 2, without catheter.
FIG. 4—ditto, an enlarged axonometric view of fragment B.
FIG. 5—ditto, an enlarged view of fragment A.

The partition 17 accommodates a sleeve 21 with a central opening 22 (FIG. 3) coaxial with the conveying line 2 (FIG. 2).

Analogously positioned is a sleeve 23 in the cover 20. Provided on a lower end 24 (FIG. 4) of the sleeve 21 are projections 25 against which the drainage pipe 3 is thrust such that a space 26 between the pipe 3 and the catheter 4 communicates with the chamber 19 (FIG. 2) of the body 16 (as shown by arrows C in FIG. 4).

The proximal end of the pipe 3 is telescoped into the chamber 19 via tapered opening 27 of the sleeve 23 having a top portion 28 shaped as a truncated cone while the tapered opening 27 is coaxial with the line 2. In so doing, the top portion 28 of the sleeve 23 has a small thickness and, when manufactured from polymeric materials, acquires elasticity which provides for its easy and hermetic coupling with the pipe 3.

For precluding the formation of stagnant pockets of powder at the time of spraying, the catheter 4 has a flared end 29 (FIG. 5) ensuring a tight coupling of of an outlet end 30 of the sprayer 1 (FIG. 2) with the catheter 4.

The cover 20 has in its bottom an opening 31 (there may be several such openings) closed with a filter 32, say, a bactericidal one.

The herein disclosed device for administering powdered substance operates in the following manner.

The pipe 3 is introduced, with the aid of a hollow stylet and under X-raying, into the cavity of tubercular cavern and mounted in the patient's body for the entire duration of the course of treatment with the aid of any suitable fixation means (not shown in the drawings).

The stylet structure enables one to perform trial aspiration of the destructive cavity of the cavern of the lung at the moment of introduction of the pipe 3 owing to the connection of the stylet to vacuum suction means. Following the withdrawal of the stylet, an X-ray contrast drain is introduced in the pipe 3 to preclude the possibility of pneumothorax, as well as to define the position of the pipe 3 in the cavern in the course of treatment.

Then, the catheter 4 is placed in the opening of the sleeve 21 of the means 15. The requisite amount of powdered substance is poured into the container 11 which is then tightly closed with the cover 14 and placed in the housing 7. The body 16 is threaded to the housing 7 coupled with the cylindrical housing 6.

Prior to the spraying of powder, the drain is removed from the pipe 3 and the catheter 4 is introduced in the latter such that the pipe 3 is received in the opening 27 of the sleeve 23 until thrust against the projections 25. Thereupon, the piston 5 is moved to the topmost position for effecting the intake of air to the sprayer 1, after which the piston 5 is moved to the lowermost position. Air flows at a high rate around the container 11 with powdered substance to capture part of the substance from the container 11 owing to rarefaction developed at the outlet end 10 of the sprayer 1 and move said substance along the catheter 4 to the cavity of tubercular cavern.

The cycle of delivering the powdered substance may be repeated many times over until all of the substance from the container 11 is injected into the cavern cavity.

Upon completion of the procedure, the catheter 4 is removed from the pipe 3 and from the means 15. The pipe 3 is plugged with the X-ray contrast drain while the used container 11 ids removed from the device, to which end the housing 7 of the sprayer 1 is detached from the housing 6.

The herein disclosed device for administering powdered substances into the patient's organism is noted for the following advantages.

All of the parts and assemblies of the device according to the invention are such that they can be made from polymeric material; they are readily adaptable to manufacture, thereby rendering their manufacture simpler and obviating abrupt junctions between parts that might cause the sticking of powder and clogging of the conveying line.

The structure of the herein disclosed device provides for its repeated use throughout the course of treatment of a single patient, reduces the time between repeated punctures and provides the possibility of daily administering of powdered substance.

The patient is saved from repeated surgical traumas caused by puncturing the tissues; the overall dose of X-ray irradiation is reduced; the possibility of the personnel getting infected is ruled out.

The device according to the present invention for administering powdered medicinal substance into the patient's organism, in particular, into the cavity of tubercular cavern, will help sharply increase the efficiency of treating patients suffering from cavernous tuberculosis, reduce the time of treatment and of the patients' stay in hospital and, therefore, reduce the cost of treatment, speed up the recovery of patients to useful activities and to preclude the emergence of new cases of tuberculosis.

What is claimed is:

1. A device for administering powdered substances into deep-seated cavities of an organism, said device comprising a sprayer having a cylinder and a piston movable within said cylinder; a conveying line series-connected to said sprayer; a drainage pipe forming part of said conveying line; a catheter in said conveying line, arranged coaxially inside said drainage pipe and adapted to be introduced into a deep-seated cavity of an organism for spraying a powdered substance thereinside;

a hollow cylindrical body connected at one end to said sprayer;
a diametral partition dividing said hollow body;
a cover adapted to close said hollow cylindrical body at an end opposite to said one end;
a first sleeve having an opening and positioned in said diametral partition such that said opening is coaxial with said conveying line;
said first sleeve receiving an end of said catheter and connecting it to said sprayer;
a second sleeve having an opening and positioned in said cover coaxially with said opening of said first sleeve;
said second sleeve retaining said drainage pipe.

2. A device as set forth in claim 1, comprising:
said cover having a bottom and at least one opening in said bottom;
a filter located on said bottom of said cover and adapted to cover all of said openings in said bottom of said cover.

* * * * *